US009144370B2

(12) United States Patent
Kato et al.

(10) Patent No.: US 9,144,370 B2
(45) Date of Patent: Sep. 29, 2015

(54) MECHANICAL STRUCTURE OF ARTICULATED SHEATH

(71) Applicants: Canon U.S.A., Inc., Melville, NY (US); The Brigham and Women's Hospital, Boston, MA (US)

(72) Inventors: Takahisa Kato, Brookline, MA (US); Ichiro Okumura, Abiko (JP); Nobuhiko Hata, Waban, MA (US)

(73) Assignees: Canon USA Inc., Melville, NY (US); The Brigham and Women's Hospital, Boston, MA (US)

( * ) Notice: Subject to any disclaimer, the term of this patent is extended or adjusted under 35 U.S.C. 154(b) by 153 days.

(21) Appl. No.: 13/834,561

(22) Filed: Mar. 15, 2013

(65) Prior Publication Data

US 2014/0243592 A1    Aug. 28, 2014

Related U.S. Application Data

(60) Provisional application No. 61/770,883, filed on Feb. 28, 2013.

(51) Int. Cl.
*A61B 1/00* (2006.01)
*A61B 1/008* (2006.01)
*A61B 1/005* (2006.01)
(Continued)

(52) U.S. Cl.
CPC ............. *A61B 1/008* (2013.01); *A61B 1/0055* (2013.01); *A61M 25/0147* (2013.01); *A61B 1/0016* (2013.01); *A61B 1/0057* (2013.01); *A61B 2017/00309* (2013.01); *A61B 2017/00314* (2013.01); *A61B 2017/00327* (2013.01)

(58) Field of Classification Search
USPC .......................... 600/121–125, 144, 150–151
See application file for complete search history.

(56) References Cited

U.S. PATENT DOCUMENTS

| 4,686,963 A | * | 8/1987 | Cohen et al. ................. 600/141 |
| 5,681,263 A | | 10/1997 | Flesch |
| 6,858,005 B2 | | 2/2005 | Ohline et al. |

(Continued)

FOREIGN PATENT DOCUMENTS

| CN | 203204237 U | 9/2013 |
| JP | 2007252560 A | 10/2007 |
| JP | 2009112538 A | 5/2009 |

OTHER PUBLICATIONS

Breedveld et al.,"A New, Easily Miniaturized Steerable Endoscope", IEEE Engineering in Medicine and Biology Magazine, Nov./Dec. 2005, pp. 40-47.

(Continued)

*Primary Examiner* — Matthew J Kastejna
(74) *Attorney, Agent, or Firm* — Canon USA Inc. IP Division

(57) ABSTRACT

A sheath apparatus includes, a plurality of node rings configured to be tilted with respect to each other, each node ring defining a substantially cylindrical wall and having at least one hole passing through said cylindrical wall, the plurality of node rings being arranged next to each other along a linear axis such that consecutive node rings contact each other at a contact plane; a manipulating wire going through the holes in said stacked node rings; and a position restoring component configured to restore said stacked node rings from a tilted position to an original position, wherein said position restoring component is located inside or outside of the stacked node rings.

9 Claims, 13 Drawing Sheets

(51) Int. Cl.
*A61M 25/01* (2006.01)
*A61B 17/00* (2006.01)

(56) References Cited

U.S. PATENT DOCUMENTS

| | | | |
|---|---|---|---|
| 6,916,335 | B2 | 7/2005 | Kanji |
| 7,591,783 | B2 * | 9/2009 | Boulais et al. ............... 600/142 |
| 7,785,252 | B2 | 8/2010 | Danitz et al. |
| 8,021,293 | B2 | 9/2011 | Dejima et al. |
| 8,292,803 | B2 | 10/2012 | Watanabe |
| 8,617,102 | B2 | 12/2013 | Moll et al. |
| 2003/0045778 | A1 | 3/2003 | Ohline et al. |
| 2007/0219581 | A1 | 9/2007 | Dohi et al. |
| 2008/0255422 | A1 | 10/2008 | Kondoh et al. |
| 2008/0281293 | A1 | 11/2008 | Peh et al. |
| 2008/0287741 | A1 | 11/2008 | Ostrovsky et al. |
| 2009/0062606 | A1 | 3/2009 | Ueda et al. |
| 2009/0105542 | A1 | 4/2009 | Kitagawa et al. |
| 2010/0010309 | A1 | 1/2010 | Kitagawa |
| 2010/0168519 | A1 | 7/2010 | Matsuo |
| 2012/0078053 | A1 | 3/2012 | Phee et al. |
| 2014/0005683 | A1 | 1/2014 | Stand et al. |

OTHER PUBLICATIONS

Szewczyk et al.,"An Active Tubular Polyarticulated Micro-System for Flexible Endoscope", pp. 1-10.

Xu et al.,"System Design of an Insertable Robotic Effector Platform for Single Port Access (SPA) Surgery", The 2009 IEEE/RSJ International Conference on Intelligent Robots and Systems, Oct. 2009, pp. 5546-5552.

* cited by examiner

DISTAL END
(surface 12)

PROXIMAL END
(surface 13)

MECHANICAL STRUCTURE OF ARTICULATED SHEATH

CROSS-REFERENCE TO RELATED APPLICATIONS

This application claims priority from Provisional Application No. 61/770,883 filed 28 Feb. 2013, the disclosure of which is hereby incorporated by reference herein in its entirety.

BACKGROUND

1. Field

The disclosure of this application relates generally to medical devices and in particular to an articulated sheath applicable to remote robotic manipulation of surgical tools and instruments, such as endoscopes.

2. Related Art

Endoscopic surgical instruments and tools are well known and continue to gain acceptance in the medical field. An endoscopic instrument or tool generally includes a rigid or flexible tube commonly referred to as a sleeve or sheath. One or more channels extend along (typically inside) the sheath to allow access to end effectors located at a distal end of the sheath. Control mechanisms located at a proximal end of the sheath are configured to enable remote manipulation of the end effectors via the one or more channels. Accordingly, the mechanical structure of the sheath plays a key role in ensuring flexible access to end effectors, while protecting delicate organs and tissues of a patient. As used herein and elsewhere in the art of endoscopic medical devices, the term "end effector" refers to the actual working part of a surgical instrument or tool.

Endoscopic surgical tools may include clamps, graspers, scissors, staplers, needle holders, and other like tools, which serve to manipulate body parts (organs or tissue) during examination or surgery. Endoscopic instruments primarily include a light delivery system which serves to illuminate a body part under inspection, and an imaging system which serves to observe the body part under inspection. In a typical endoscopic light delivery system, the light source is located outside the patient's body and the light is delivered via an optical fiber system. In an endoscopic imaging system, an objective lens located at the distal end of the sheath transmits the image, formed by collected light, via a bundle of optical fibers to a viewing device or sensor located at the proximal end of the sheath. An example of a surgical endoscopic instrument includes a laparoscope, but many more exist.

Current endoscopic technology endeavors to reduce the amount of negative side effects and increase patient comfort, by providing minimally invasive surgery (MIS). However, one of the major shortcomings in the current state of the art of endoscopic tools is the lack of dexterity and sensitivity offered to health professionals (endoscopists and surgeons) who perform endoscopic procedures.

In particular, many conventional endoscopic instruments with rigid or flexible sheaths prevent the surgeon or endoscopist from easily maneuvering endoscopic tools and instruments due to the rigidity of the mechanical structure of the sheath. More importantly, rigid or flexible sheaths prevent the surgeon from obtaining an accurate feeling (feedback feeling) of the amount of pressure or force exerted by an end effector on the organ or tissue under inspection or operation.

For example, patent application publication US 2008/0287741 disclosed by Ostrovsky et al., describes an articulating mechanism for use in an endoscope or a catheter. The mechanism includes a series of stacked links disposed adjacent to one another and movable with respect to each other. Pull-wires provide tension and hold the staked links together while also allowing for controlled bending of the distal portion by movement of one or more of the pull-wires. Notably, the stacked links have no restoring force at the joint. The pulling of the wire will not distribute the bending forces evenly among the multiple links. The bending angles at each joint will be uneven at different joints. Thus, this sheath will not be controlled to a uniform curvature.

Another example, set forth in U.S. Pat. No. 7,785,252 to Danitz et al., discloses an articulating sheath for flexible instruments. The sheath having an elongated shaft with proximal and distal sections includes multiple pairs of links. The sheath also includes one or more sets of cables connecting the links of at least one discrete pair to another, such that movement of one link of the connected pair causes corresponding relative movement of the other link of the pair. Movement of the proximal section results in corresponding movement of the distal section. In this patent, flexible hinges receive compressive force by wire (cable) tension. To withstand the compressive force flexible hinges must be rigid in the axial direction, and the stiffness is designed to be large. This stiffness requires the wires tension to be large, which makes it difficult for the endoscopist or surgeon to obtain an appropriate feel of the amount of force being exerted by an end effector on the organ or tissue of a patient. In addition, when the mechanical structure of the sheath is controlled by a motor, it requires the motor to be large. For surgeries at the medical site, a large motor is a cause to hinder the precise and accurate maneuvers of surgeons, or becomes a cause of fatigue for the operator.

As used herein, the term "stiffness" refers to the rigidity of an object or material. Stiffness can be determined by the extent or amount to which an object or material resists deformation (e.g., bending, stretching or compression) in response to an applied force or tension. Stiffness may be considered as complementary or opposite to flexibility or pliability. That is, the more flexible an object or material is, the less stiff it is. In mathematical terms, the stiffness K of an object or material is a measure of its resistance to deformation in response to an applied force F. For an object having a single degree of freedom (e.g., one direction of bending) the stiffness is defined as $K=F/\delta$, where $\delta$ is the displacement produced by the applied force. In the International System of Units, stiffness is measured in newtons per meter, while in English Units stiffness is measured in pounds (lbs) per inch. Although an object may be submitted to more than one deformation at a time (e.g., bending and stretching simultaneously), for the sake of simplicity, the discussions in the present application consider deformation of an object and its stiffness thereof in only one degree of freedom at a time.

Patent application publication US 2012/0078053 disclosed by Phee et al., discloses a Robotic system for Flexible Endoscopy. According to Phee et al., it is possible to implement a sheath having a fixed bending radius or a sheath having different bending radius each with the different length, so that an endoscope can be easily manipulated a gastrointestinal (GI) track to diagnose GI diseases.

In highly delicate surgical operations, such as neurosurgery, it is necessary to avoid the contact of endoscope or any other surgical tools with the critical brain tissues and nerves in the periphery of the lesion. To that end, it is necessary to maneuver with precisely controlled shape of the sheath and to know with a high degree of certainty how much force or tension is being applied to an end effector. It is also necessary to view in detail the lesion from various directions, often even from an opposite direction from which the endoscope is inserted. In this manner, the operation can be performed without damaging delicate structures located nearby the organ or tissue being operated. To that end, it is necessary to be able to easily bend the sheath to a controlled shape in all directions and in any location, without exerting excessive force.

SUMMARY

According to at least one embodiment of the present application, certain aspects of the present invention are defined in the appended claims. Advantageously, in accordance with the various embodiments described below, a mechanical sheath structure with a controlled shape in all directions and capable of bending any location without exerting excessive force is disclosed.

According to a first aspect of the present invention, a sheath apparatus includes, a plurality of node rings configured to be tilted with respect to each other, each node ring defining a substantially cylindrical wall and having at least one hole passing through said cylindrical wall, the plurality of node rings being arranged next to each other along a linear axis such that consecutive node rings contact each other at a contact plane; a manipulating wire going through the holes in said stacked node rings; and a position restoring component configured to restore said stacked node rings from a tilted position to an original position, wherein said position restoring component is located inside or outside of the stacked node rings.

Further features of the present invention will become apparent from the following description of exemplary embodiments with reference to the attached drawings.

DETAILED DESCRIPTION

Figure 1A:
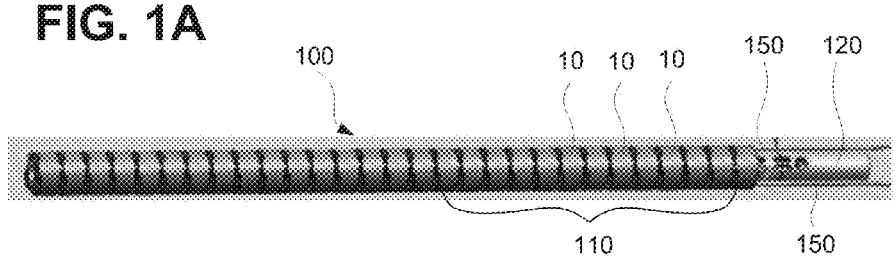
FIGS. 1A and 1B illustrate an exemplary configuration of a mechanical structure of an articulated sheath, in accordance with an embodiment of the present invention.

In the following description, reference is made to the accompanying drawings which are illustrations of embodiments in which the disclosed invention may be practiced. It is to be understood, however, that those skilled in the art may develop other structural and functional modifications without departing from the novelty and scope of the instant disclosure.

In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage device such as a magnetic or optical disk and disk drive for storing information and instructions, an optional user output device such as a display device (e.g., a monitor) for displaying information to the computer user, an optional user input device including alphanumeric and function keys (e.g., a keyboard) for communicating information and command selections to the processor, and an optional user input device such as a cursor control device (e.g., a mouse) for communicating user input information and command selections to the processor.

As will be appreciated by those skilled in the art, the present examples may be embodied as a system, method or computer program product. Accordingly, some examples may take the form of an entirely hardware embodiment, and entirely software embodiment (including firmware, resident software, micro-code, etc.) or an embodiment combining software and hardware aspects that may all generally be referred herein as a "circuit", "module" or "system". Further, some embodiments may take the form of a computer program product embodied in any tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that can direct a computer or other programmable data processing apparatus to function in a particular manner, such that the instructions stored in the computer-readable media constitute an article of manufacture including instructions and processes which implement the function/act/step specified in the flowchart and/or block diagram.

It should be understood that if an element or part is referred herein as being "on", "against", "connected to", or "coupled to" another element or part, then it can be directly on, against, connected or coupled to the other element or part, or intervening elements or parts may be present. In contrast, if an element is referred to as being "directly on", "directly connected to", or "directly coupled to" another element or part, then there are no intervening elements or parts present. When used, term "and/or", includes any and all combinations of one or more of the associated listed items, if so provided.

Spatially relative terms, such as "under" "beneath", "below", "lower", "above", "upper", "proximal", "distal", and the like, may be used herein for ease of description to describe one element or feature's relationship to another element(s) or feature(s) as illustrated in the various figures. It should be understood, however, that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, a relative spatial term such as "below" can encompass both an orientation of above and below. The device may be otherwise oriented (rotated 90 degrees or at other orientations) and the spatially relative descriptors used herein are to be interpreted accordingly. Similarly, the relative spatial terms "proximal" and "distal" may also be interchangeable, where applicable.

The terms first, second, third, etc. may be used herein to describe various elements, components, regions, parts and/or sections. It should be understood that these elements, components, regions, parts and/or sections should not be limited by these terms. These terms have been used only to distinguish one element, component, region, part, or section from another region, part, or section. Thus, a first element, component, region, part, or section discussed below could be termed a second element, component, region, part, or section without departing from the teachings herein.

The terminology used herein is for the purpose of describing particular embodiments only and is not intended to be limiting. As used herein, the singular forms "a", "an", and "the", are intended to include the plural forms as well, unless the context clearly indicates otherwise. It should be further understood that the terms "includes" and/or "including", when used in the present specification, specify the presence of stated features, integers, steps, operations, elements, and/or components, but do not preclude the presence or addition of one or more other features, integers, steps, operations, elements, components, and/or groups thereof not explicitly stated.

In describing example embodiments illustrated in the drawings, specific terminology is employed for the sake of clarity. However, the disclosure of this patent specification is not intended to be limited to the specific terminology so selected and it is to be understood that each specific element includes all technical equivalents that operate in a similar manner.

Exemplary embodiments will be described below with reference to the several drawings, wherein like reference numerals designate identical or corresponding parts throughout the several views and embodiments.

(First Embodiment)

Figure 1B:
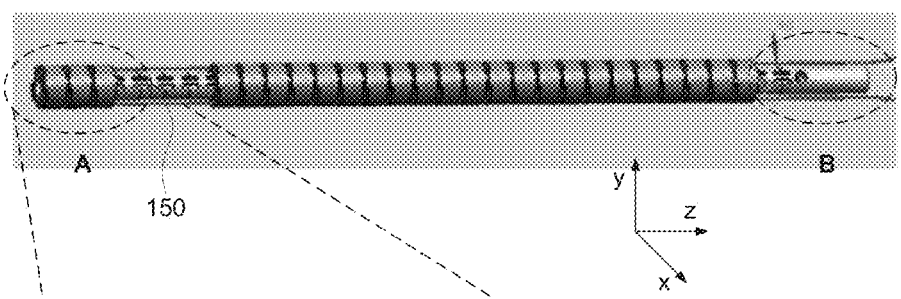
Figure 1C:
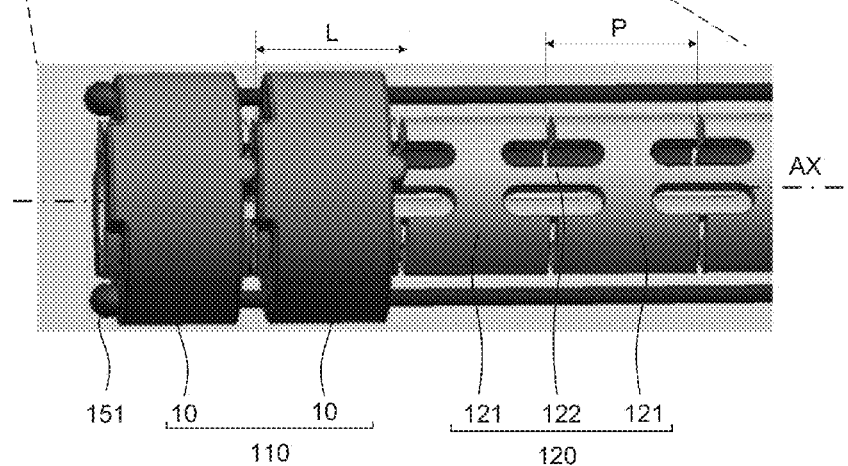
FIG. 1C illustrates an enlarged view of relevant parts in the mechanical structure of an articulated sheath, in accordance with an embodiment of the present invention.

FIGS. 1A through 1C illustrate an exemplary configuration of a basic mechanical structure of an articulated sheath 100, in accordance with an embodiment of the present invention. As used herein, the term "basic mechanical structure" refers to a basic building block or smallest unit or sheath section of the articulated sheath 100 necessary to obtain a minimal articulation (bend) along an angle of plus/minus theta ($\theta$) with respect to a central axis (linear axis) AX of the articulated sheath 100. As illustrated in FIG. 1A, an articulated sheath 100 includes an outer body 110 made of a plurality of node rings 10, and inner body 120 arranged inside the outer body 110, and a plurality of wires 150 passing through holes in the plurality of node rings 10.

As illustrated in FIG. 1B, the plurality of node rings 10 of the outer body 110 are stacked or arranged in series one upon another; and the wires 150 pass through holes formed in the wall of each node ring 10. In this manner, the wires 150 extend from a distal end A to a proximal end B of the articulate sheath 100.

FIG. 1C illustrates an enlarged view of the distal end A in the mechanical structure of the articulated sheath 100. As shown in FIG. 1C, the outer body 110 is formed of plural cylindrical tubular node rings 10 arranged in series one after another around the inner body 120. The inner body 120 is formed of a single tubular structure which works as center spring. The center spring of the inner body 120 includes a plurality of cylindrical units 121 connected to each other by bendable hinges 122 (bendable links). The cylindrical units 121 and bendable hinges 122 are part of a single structural entity machined to from the cylindrical units 121 and bendable hinges 122 arranged in series at a predefined pitch P. The pitch P is substantially equal to a total length L of each node ring 10. The wires 150 are engaged with a node ring 10 at the distal end of the sheath (or at any other position) by a locking bead 151. To maintain the plurality of node rings 10 aligned and in close contact with each other, the wires 151 extend through holes 14 formed in the cylindrical wall of the node rings 10 from the distal end A to the proximal end B of the sheath 100.

There is not limitation in terms of materials or method of fabrication that can be used to manufacture the different parts of an articulated sheath 100. It is envisioned that persons having ordinary skill in the art will be familiar with various methods of fabrication and available materials applicable to desired uses of the structures disclosed herein. In certain prototype or experimental examples, the inventors herein have used materials and methods of fabrication that are currently commercially available. However, other suitable materials and methods of fabrication may become available in the future. In one such example, since the inner body 120 is used as an element that serves to restore the shape of the sheath 100 to its original unbent position, the inner body 120 may be made of galvanized iron, stainless steel, or shape memory alloys (SMRs). SMAs are metals that "remember" their original shapes, and thus are useful for forming actuators that change shape, stiffness, position or the like, and are required to return to its original shape, stiffness, position or the like. Nickel-titanium alloys have been found to be particularly useful SMAs, but others are available. Accordingly, SMAs may be particularly advantageous for forming the inner body 120 of sheath 100 due to the SMAs ability to repeatedly flex or bend without breaking. The wires 150 may be sterilized steel wire or other known composite-based wire. More specifically, for node rings, materials such as stainless steel, Nickel-Titanium NiTi (shape memory alloy), PEEK (polyetheretherketone), PET (polyethylene terephthalate) are some of the examples that can be used. For guide wires, stainless steel, NiTi (shape memory alloy), Nylon, PE (Polyethylene), PVDF (Polyvynylidene Difluoride) are some of the examples. For the center spring (inner body 120), NiTi (Shape memory alloy), stainless steel, piano wire (music wire), phosphor bronze, BeCu (beryllium copper), spring steel are some additional examples of materials that can be used.

Figure 2A:
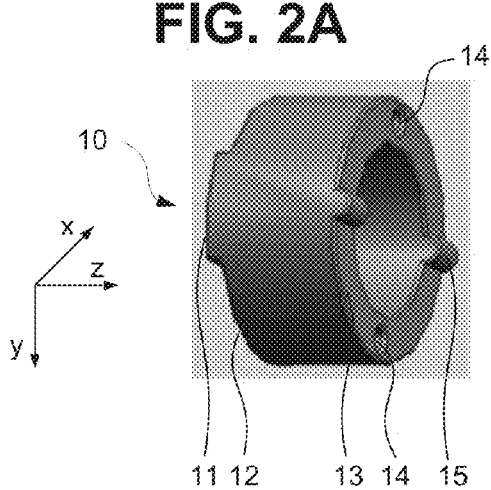
FIGS. 2A and 2B illustrate a perspective and a side view of a node ring of an articulated sheath.
Figure 2B:
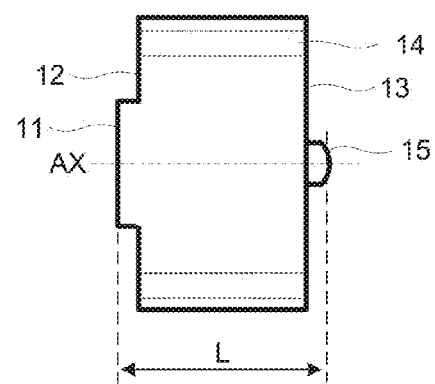
Figure 2C:
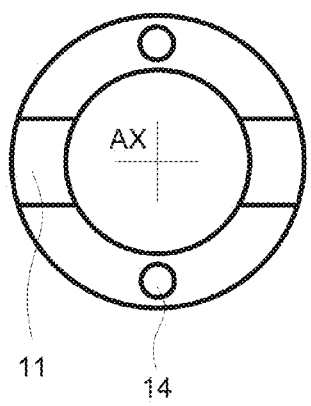
FIGS. 2C and 2D illustrate distal and proximal ends of the node ring illustrated in FIG. 2A.
Figure 2D:
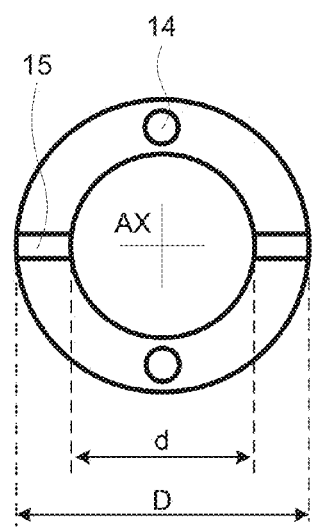

FIGS. 2A through 2D illustrate in further detail the structure of node rings 10. FIG. 2A shows a three-dimensional (perspective) view of a single tubular node ring 10; FIG. 2B shows a side (longitudinal) view of the node ring 10; FIG. 2C shows a plane view seen from a distal end (distal view) of node ring 10; and FIG. 2D shows a plane view seen from a proximal end (proximal view) of a node ring 10. Specifically, as illustrated in these figures, each node ring is formed as a cylindrical tubular structure having a predetermined length L, and inner diameter d and outer diameter D which together form a circumferential wall therebetween. Notably, the node ring 10 includes, on its distal end thereof, a first surface 12 which includes a flat protrusion 11, and on its proximal end thereof a second surface 13 which includes a curved protrusion 15. Holes 14 extend from the first surface 12 to the second surface 13 along the circumferential wall of node ring 10. A longitudinal distance between the flat protrusion 11 on the first surface to the apex of the curved protrusion 15 on the second surface 13 defines the length L of each node ring 10.

As illustrated in FIG. 2C, a plurality of holes 14 and flat protrusions 11 may be formed on the first surface 12 of each node ring 10. In FIG. 2C, each hole 14 is disposed at approximately 90 degrees with respect to the center surface of flat protrusion 11. In practice however, the holes 14 may be arranged at any distance from the flat protrusions 11. Similarly, as illustrated in FIG. 2D, a plurality of holes 14 and curved protrusions 15 may formed on the second surface 13 of each node ring 10. In FIG. 2D, each hole 14 is disposed at 90 degrees with respect to a curved protrusion 15. In practice however, the holes 14 may be arranged at any distance from the curved protrusions 15 on the second surface 13, along the circumferential wall of tubular node ring 10.

Figure 3A:
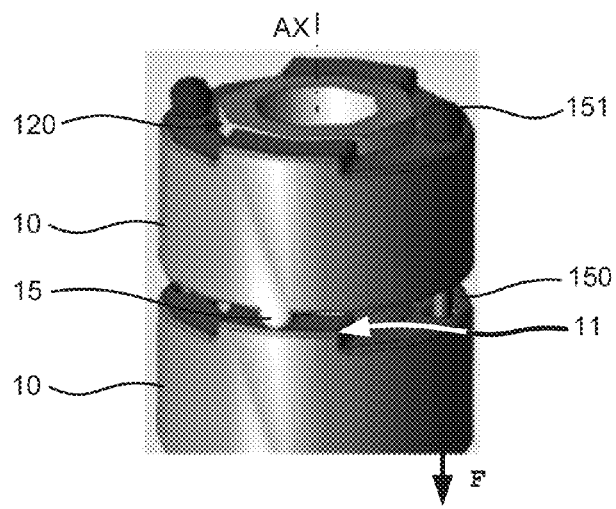
FIGS. 3A through 3D illustrate motion control for actuating the mechanical structure of the articulated sheath.
Figure 12:
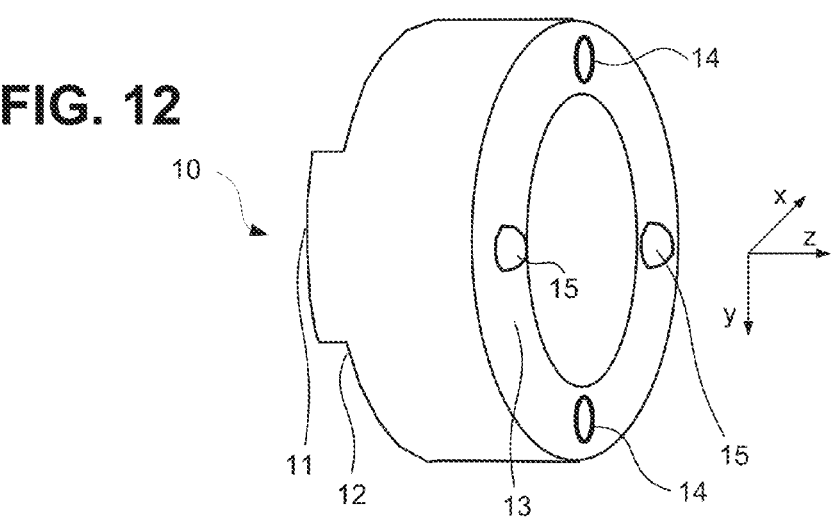
FIG. 12 illustrates a node ring having curved protrusions of hemispherical shape.

Turning now to FIGS. 3A through 4C, motion control for actuating the mechanical structure of the articulated sheath 100 is described. Initially, FIG. 3A illustrates a three-dimensional view of a distal end of an exemplary sheath 100. In FIG. 3A, two consecutive node rings 10 are arranged such that the consecutive node rings contact each other at a contact plane orthogonal to the linear axis AX. A contact portion between the two consecutive node rings 10 is the portion of curved protrusion 15 in one node ring 10 which contacts the flat protrusion 11 of an adjacent node ring 10. Expressed in another way, the contact portion between the two consecutive node rings 10 is the portion the flat protrusion 11 of one ring 10 which is in direct physical contact with the curved protrusion 15 in an adjacent node ring 10. When the curved protrusion 15 is a cylindrical protrusion, as shown in FIG. 3A, the contact portion is essentially a contact line defined by the apex of curved protrusion 15 in direct contact with the flat protrusion 11. When the curved protrusion 15 is a hemispherical protrusion, as shown in FIG. 12, the contact portion is essentially a contact point defined by the apex of curved protrusion 15 in direct contact with the flat protrusion 11. In either case, the contact line or contact point will be on a contact plane orthogonal to the linear axis AX of the sheath 100.

Figure 3B:
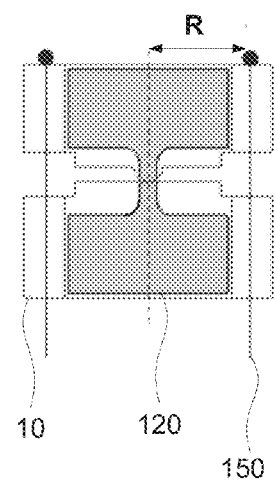
Figure 3C:
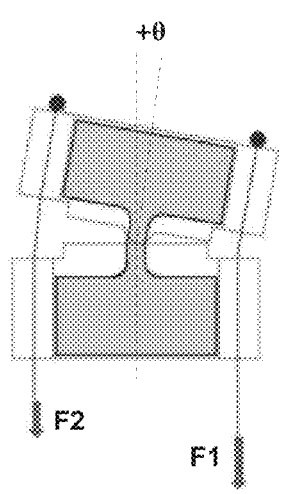
Figure 3D:
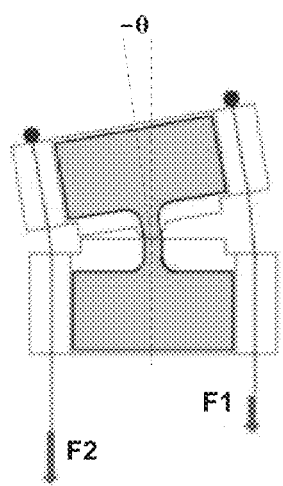

Turning now to the bending movement between two consecutive node rings 10, it is clear from FIG. 3A that when a wire 150 is pulled in a direction parallel to the linear axis AX (axial direction), one of the node rings 10 moves with respect to the other because the contact portion between curved protrusion 15 and flat protrusion 11 of the two consecutive node rings 10 acts as a fulcrum to a pulling force F applied to the wire 150. FIGS. 3B, 3C and 3D show the bending process in an ideal configuration of the mechanical sheath disclosed herein. That is, in these figures, the contact portion and the center of the hinge are exactly at the same position along the linear axis AX. Prior to applying any bending force, however, as illustrated in FIG. 3B, when the sheath 100 is at its resting state, the wires 150 pass through holes 14 of node rings 10; and the curved protrusion 15 of a distal node ring 10 makes contact with the flat protrusion 11 of a proximal node ring 10. In this resting state, the hinges 122 of inner body 120 are not bent; and the entire sheath 100 is substantially straight and aligned along a common linear axis (sheath axis) AX. Moreover, in the resting state of FIG. 3B, the longitudinal axis of the inner body 120 and the longitudinal axis of each node ring 10 are aligned with the linear axis AX. In order to maintain the entire sheath 100 in its resting state, where the node rings 10 are arranged in close contact to each other, an initial tension T exists in both wires 150.

In order to actuate on an end effector (not shown) disposed at the distal end of the sheath 100, a force F1 pulls on a first wire 150 or a force F2 pulls on a second wire 150 towards the proximal end of sheath 100, as shown in FIG. 3C. When the force F1 pulling on the first wire 150 is larger than the force F2 pulling on the second wire 150, the difference of the two forces creates a resultant tension that tilts the first node ring 10 to an angle theta ($\theta$) with respect to axis AX. The tilted distal node ring 10 exerts a bending momentum on a hinge 122 of the center spring (inner body 120), and thus bends the hinge 122 to the side of the pulling force F1, as illustrated in FIG. 3C. In contrast, when the force F2 pulling on the first wire 150 is larger than the force F1 pulling on the second wire 150, the difference of the two forces tilts the distal node ring 10 an angle of minus theta with respect to axis AX. The tilted distal node ring 10 exerts a bending momentum on the hinge 122 of the center spring (inner body 120), and bends the hinge 122 to the side of the pulling force F2, as illustrated in FIG. 3D.

For convenience of notation, the angle theta in FIG. 3C will be considered positive, and the angle theta in FIG. 3D will be considered negative. That is, as used herein, tilting the a node ring 10 in a clockwise direction with respect to the sheath axis AX will be considered a tilt with a positive angle; and tilting a node ring 10 in a counter clockwise direction with respect to the axis AX will be considered a tilt with a negative angle.

Notably, the forces pulling on the first and second wires 150 both create a tension that presses on the contact portion between the curved protrusion 15 of the distal node ring 10 and the flat protrusion 11 of the proximal node ring 10. However, due to its curved shape, the curved protrusion 15 simply rolls on the plane surface of the flat protrusion 11. When the contact point occurs at (or substantially near) the center (point) of bending of the hinge 122, there is minimal or no slippage between the curved surface of the curved protrusion 15 and the plane surface of the flat protrusion 11. In other words, there is minimum or no slippage between the curved surface of the curved protrusion 15 and the plane surface of the flat protrusion 11, when the apex of the curved protrusion 15 is orthogonally aligned with the longitudinal midpoint of hinge 122. To that end, the length L of each node ring 10 is preferably made equal to the pitch P (distance between the longitudinal midpoints of two consecutive hinges 122). In this manner, the apex of the curved protrusion 15 can be precisely aligned with the location of least resistance to bending of each hinge 122 in the axial direction of the sheath 100. Therefore, the tilting process requires minimal force in order to exert a bending momentum on the hinge 122. Moreover, the force actuating on the wire 150 easily pivots the node ring 10, therefore the applied force is translated to the sheath curvature in a highly efficient manner.

More specifically, taking into account the pulling forces F1 and F2 illustrated in FIGS. 3C and 3D, the difference between these forces can easily bend the sheath 100 theta degrees or radians in either a clockwise direction or a counter clockwise direction with respect to the axis AX, based on the following expression (1):

$$\theta = R^* |F1 - F2|/K \tag{1}$$

In expression (1), K is the bending stiffness of the hinge 122; R is the distance between the axial center (axis AX) of sheath 100 and the wire 150 exerting the larger force (ideally, both wires should be located at the same distance R from the axis AX); F1 is the force exerted by a first wire 150; F2 is the force executed by a second wire 150; and theta is the resultant bending angle of the hinge 122 with respect to the axis AX. Any curvature of the sheath 100 can be controlled by the tension exerted by the first and second wires 150, and the required force can be quantified by expression (1).

Figure 4A:
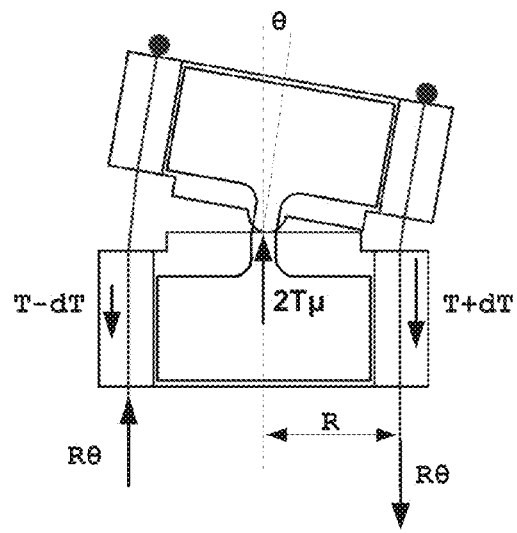
FIGS. 4A through 4C illustrate an exemplary manner in which the articulated sheath is bent.
Figure 4B:
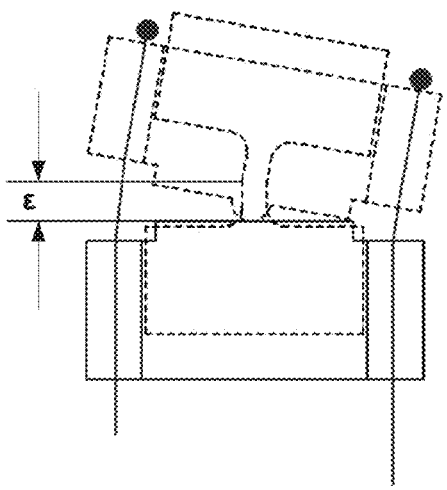
Figure 4C:
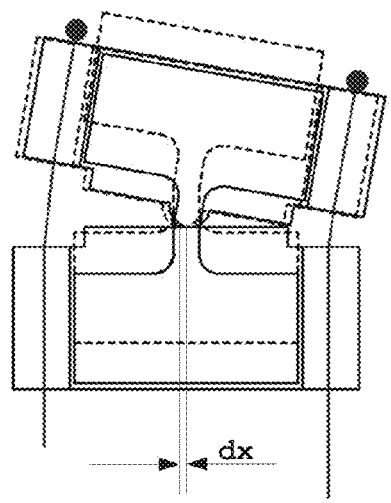

Turning now to FIGS. 4A to 4C a more specific description is provided as to the manner in which the sheath 100 is bent. As illustrated in FIG. 4A, when the wires 150 are actuated in order to bend the sheath 100, both wires 150 actuate on the distal end of a distal node ring 10, and predetermined forces (F1 and F2 described above) exert tension towards the proximal end of sheath 100. The wire 150 pulling with the larger force determines the direction of tilt of the distal node ring 10. For example in the case of FIG. 4A, both wires 150a and 150b may be pulled by a non-illustrated actuator. In turn, these pulling forces exert a longitudinal tension T towards the proximal end of sheath 100. However, in order to bend sheath 100, one wire must exert a larger tension than the other. In FIG. 4A, wire 150a exerts a larger tension than wire 150b, and thus a difference tension dT exits. Therefore, wire 150a exerting a tension T+dT causes a tilt of the distal node ring 10 in a clockwise direction. As a result, hinge 122 of inner body 120 bends with respect to the sheath axis AX an amount of theta (degrees or radians).

Ideally, as discussed above, the contact portion between the curved protrusion 15 and the flat protrusion 11 is in the same longitudinal location in the axial direction as the center of bending of hinge 122. And, when the tilt of the distal node ring 10 occurs, the tension exerted by the first wire 150a is T+dT, and the tension of wire 150b is T−dT. Where T is the initial tension applied by each wire to maintain all of the elements of sheath 100 in place; and dT is the tension applied to bend the sheath in one direction. However, the initial tension towards the proximal end of sheath 100 causes an equal but opposite pressing force at the apex of the curved protrusion 15 in contact with the flat protrusion 11 (at the contact portion). That is, the tension 2T towards the proximal end of sheath 100 causes an opposite force 2T towards the distal end. Therefore, in order to bend the sheath 100 at a point where two consecutive node rings 10 meet, a force momentum greater than the sum of resisting forces must be applied. That is the force momentum for bending must overcome the tension that keeps the sheath 100 in place plus the stiffness of hinge 122.

FIG. 4B shows the configuration of the mechanical structure of sheath 100 in a less ideal state of having a small longitudinal displacement between the outer node rings and the inner spring (inner body 10). The small displacement during bending of the sheath 100, and is caused by various manufacturing errors and assembly errors within a certain tolerance. For the sake of determining the limit of undesired displacement between the outer node rings and inner spring, the difference in longitudinal position between the inner body 120 with respect to the outer body 110 is referred to as epsilon (ε), as illustrated in FIG. 4B.

In addition, as the distal node ring 10 tilts, curved protrusion 15 slips (moves) on the flat protrusion 11. This minute movement is referred to as dx. As shown in FIG. 4C, dx is a lateral movement, and it is affected by friction between the curved protrusion 15 and the flat protrusion 11. Specifically, by overlaying FIG. 4A and FIG. 4B, the resultant FIG. 4C illustrates the amount of slippage dx in a direction orthogonal to the axis AX and to the left in this particular figure. The amount of lateral slippage dx can be quantified by taking into account the friction coefficient μ at the point of contact between curved protrusion 15 and flat protrusion 11, the distance R from axis AX to the wire 150, the friction force 2T between the curved protrusion 15 and the flat surface 11, the bending stiffness K of the hinge 122, and the longitudinal translation distance D that the wire 150 should be displaced in order to exert a bending momentum θ*K on hinge 122 to bend the hinge 122 θ degrees or radians, as follows:

The longitudinal translation distance D or length of the wire 150 to be pulled to achieve a tilt of an angle θ in node ring 10 can be derived from basic trigonometry and determined to be R*θ (hereinafter "Rθ"). That is, Rθ is defined as the length of the wire 150 to be pulled to achieve a tilt of an angle θ in the distal node ring 10.

dx is the distance the curved protrusion 15 slips on the flat protrusion 11, or the lateral movement of the point of contact between these two protrusions, as the node ring 10 tilts an angle of θ either in a clockwise or counter clockwise direction. Therefore, the following expressions (2a) and 2b) are defined, as the curved protrusion 15 slips and the contact point changes when the distal node ring 10 tilts, as follows:

$$dx/\epsilon = \theta \tag{2a}$$

$$dx/\theta = \epsilon \tag{2b}$$

dx/Rθ is the pivot leverage ratio. The ratio of [necessary slippage at the contact point between curved protrusion 15 and flat surface 11] to [the wire pull distance Rθ for the slippage].

Given a friction coefficient μ at the contact point of the apex of the curved protrusion 15 with the flat protrusion 11, the friction force working parallel to the flat surface 11 is 2Tμ in the direction opposite to the pulling tension of wires 150.

The effective momentum K*θ to bend the hinge 122 (bending momentum) is equal to the momentum created by the wire tension minus the momentum created by the friction force. For the momentum generated by the wire tension, the tension exerted by each of the two wires 150 on node ring 10 must be considered, as follows:

(T+dT)*R−(T−dT)*R, which is simplified to expression (3) below $$2R^*dT \tag{3}$$

The momentum generated by the friction force, on the other hand, can be derived by taking into consideration that the effective exerted force in the direction opposite to the wire tension is [the friction at the contact point] multiplied times [the pivot ratio] and further multiplied by [the distance R].

By multiplying the pivot leverage ratio times the friction force at the contact point between curved protrusion and flat protrusion 11, one can obtain the equivalent tension force at the wire 150. Therefore, the converted friction force to the wire tension pull force is defined by expression (4):

$$2T\mu * dx/R\theta \tag{4}$$

The negative momentum generated by the effective friction force is R multiplied by expression (4), which yields the simplified expression (5), as follows:

$$2T\mu * dx/\theta \tag{5}$$

Now, therefore, the effective momentum for bending the hinge 122 of inner spring will be obtained from expressions (3) and (5), which results in expression (6)

$$2dT*R - 2T\mu * dx/\theta = K\theta \tag{6}$$

Now, replacing expressions (2a) or (2b) into (6), the result is expression (7)

$$2(R\,dT - T\mu*\epsilon) = \theta K \tag{7}$$

Since the momentum θ K must be greater than 0 to be able to bend the hinge 122 of the center spring (inner body 120), from equation (7), the following first conditional expression (9) is established, as follows:

$$R\,dT - T\mu*\epsilon > 0 \tag{8a}$$

or $$R\,dT > T\mu*\epsilon \tag{8b}$$

which yields $$dT/T > \mu\epsilon/R \tag{9}$$

Since T−dT cannot be a negative value, dT/T will not be larger than 1. Therefore, expression (9) can be rewritten as expression (9b)

$$1 > \mu\epsilon/R \tag{9b}$$

which yields $$\epsilon < R/\mu \tag{10}$$

Notably, conditional expression (10) is the condition necessary to be satisfied for bending the hinge 122 and angle θ. If conditional expression (10) is not satisfied, sheath 100 will not bend. Specifically, when there is a large displacement of the contact portion and the center of the hinge, due to the resistance by friction, the joint will not be able to bend. For example, when R=1 mm and μ=0.5, the displacement ε must be smaller than 2 mm.

In the foregoing discussion of expressions (1) through (10), the amount of momentum generated by the tension provided by wires 150, as well as the loss of momentum due to friction have been considered. With these considerations, the sheath 100 disclosed herein has been designed for maximum efficiency with minimum applied force.

As used herein, efficiency η is defined as the ratio of output momentum to input momentum. Therefore, from expressions (3) and (5), efficiency η is given by expression (11)

$$\eta = [2R\,dT - T\mu\epsilon]/[2R\,dT]$$

$$\eta = 1 - T\mu\epsilon/(R\,dT) \tag{11}$$

Assuming that an efficiency of at least 90% is required for practical use of sheath 100 with a minimum applied force, the following conditional expression (16) is established, as follows:

$$1 - T\mu\epsilon/(R\,dT) > 0.9 \tag{12}$$

which is equivalent to $$0.1 \geq (T/dT)(\mu\epsilon/R) \tag{13}$$

or $$R/(10\mu) \geq \epsilon(T/dT) \tag{14}$$

Again, since T−dT cannot be negative, the smallest value of T/dT is 1, which implies $$T/dT \geq 1 \tag{15}$$

and $$R/(10\mu) \geq \epsilon \tag{16}$$

Conditional expression (16) provides a frame of reference for work efficiency in the bending of sheath 100. Specifically, in order for sheath 100 to effectively translate an applied tension into bending momentum, conditional expression (16) must be satisfied. Satisfying conditional expression (16) guarantees an efficiency of at least 90%.

With the above definitions and analysis, the conditional expression (10) provides that a longitudinal displacement ε smaller than R/μ is required to tilt the distal node ring 10 an angle of θ radians. On the other hand, the conditional expressions (15) and (16) provide specific conditions for determining the longitudinal displacement between the inner spring (inner body 120) and the node rings 10 of outer body 110 for an efficient operation of sheath 100.

For example, with a distance R between the axis AX and the wire 150 of about 1 millimeter (mm) and a friction coefficient μ=0.3, the limit of offset displacement ε is calculated as follows.

NUMERICAL EXAMPLES

R=1 mm, m=0.3,

When (T/dT)=1, ε≤0.333 mm,

When (T/dT)=2, ε≤0.167 mm,

When (T/dT)=5, ε≤0.067 mm,

When (T/dT)=10, ε≤0.033 mm,

The sample values above show that smaller (T/dT) tolerates larger offset displacement ε. In other words, it is more desirable for the balancing tension of T to be as small as possible. On the other hand, in a case where an uncontrolled outside force is exerted, it is desirable to maintain the balancing tension T to be a large value to resist the outside force.

In order to bend the whole structure of sheath 100 to a small radius, the ratio T/dT is small (e.g., 2). On the other hand, in order to slightly bend the structure of sheath 100 to a large radius of curvature, the ratio T/dT is large (e.g., 10). It was observed that in order to maintain the stability of the mechanical structure under various error factors and outside forces, (T/dT) is greater or equal to 2. Thus, to maintain an stable control of sheath 100 with the efficiency of η≥90%, the following conditional expression (17) more preferably holds.

$$R/(20\mu) \geq \epsilon \tag{17}$$

This means that as long as the apex of the curved protrusion 15 slips (rolls) over the flat protrusion 11, the hinge 122 of the center spring will bend an angle θ in the direction of the wire with larger tension. The actual amount of movement or slippage in the contact portion between the curved protrusion 15 and the flat protrusion 11 is minimal. Therefore, the actuator force is translated to sheath curvature highly efficiently, which in turn means that the force applied for bending can be optimized. However, the practical use of the sheath 100 will depend on the level of desired efficiency, which is determined by expressions (16) and (17).

Figure 5:
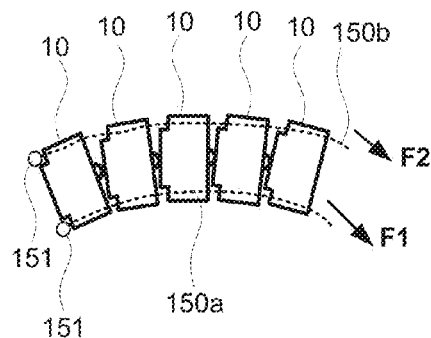
FIG. 5 illustrates an example of a basic structure of the articulated sheath.

Turning now to FIG. 5, an example is illustrated where a plurality of node rings 10 are arranged in series one after another around an inner body 120 (not shown) to form a basic structure of a sheath 100. To achieve bending, a first wire 150a and a second wire 150b are secured onto a distal node ring 10 via locking beads 151. To bend the basic structure of sheath 100 to a first direction, a first wire 150a is pulled by a non-shown actuator with a force F1 (in this case) greater than a force F2 applied to a second wire 150b. To bend the basic structure of sheath 100 in a second direction different from the first direction, the second wire 150b is pulled by the non-shown actuator with a force F2 larger than a force F1 applied to the first wire 150a. To restore the sheath 100 to its resting state (i.e., to a non curved position), the actuator(s) gradually release wires 150a and 150b, and the inner body 120 acts as an elastic spring to restore the basic section of sheath 100 to its linear or straight position. The illustration of FIG. 5 provides an example where the sheath 100 can be bent in either of two directions to form a curved shape with a variable radius. More specifically, as it can appreciated from the drawn example in FIG. 5, the length of the section of sheath 100 is determined by the number of node rings 10 necessary to obtain a desired curved shape, and the amount of tension applied to the first wire 150a (or second wire 150b) will determine the radius of curvature achieved.

Figure 6:
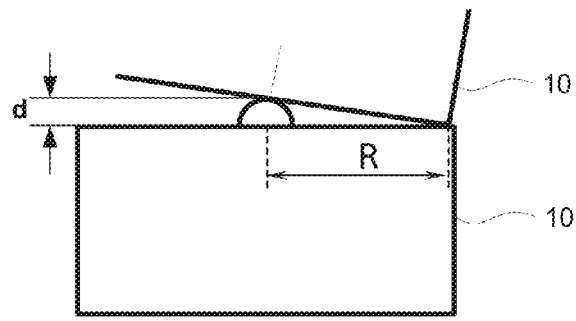
FIG. 6 illustrates exemplary parameters considered for calculating an angle of bending of the articulated sheath.
Figure 7:
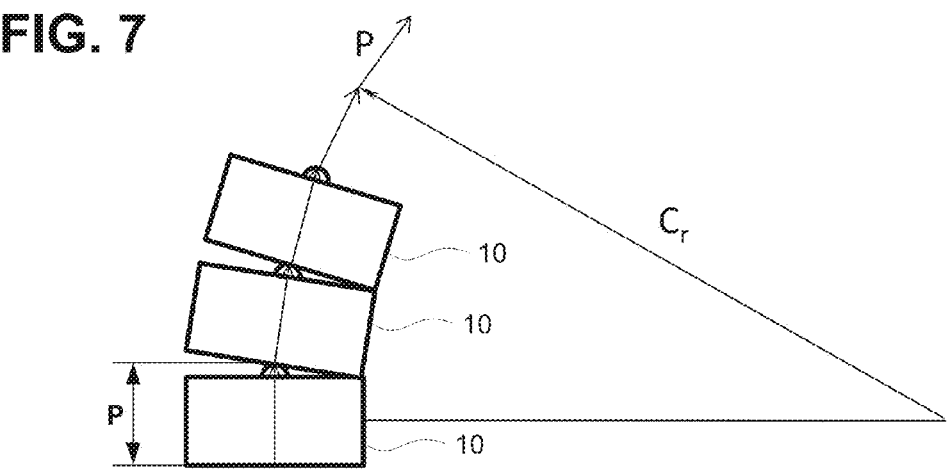
FIG. 7 illustrates exemplary parameters considered to calculate a radius of curvature for a desired number of node rings in the articulated sheath.

Referring to FIGS. 6 and 7 a description is given of an example calculation of the number node rings 10 necessary for a given bending angle theta. Specifically, FIG. 6 illustrates a simplified version of two consecutive node rings 10, where one ring 10 is tilted with respect to the other. Assuming in FIG. 6 that a maximum tilt of an angle theta has been achieved when an edge of a first node ring 10 touches the edge of and adjacent node ring 10, then theta is the maximum bending that the sheath 100 can achieve with two consecutive node rings 10. With two consecutive node rings 10, the maximum bending angle theta can be determined from the protrusion height d of the curved protrusion 15 and the distance from the protrusion contact section to the edge contact point between the two consecutive node rings 10, as follows:

$$\theta = d/R \tag{18}$$

As illustrated in FIG. 6, for the sake of simplicity, R in expression (18) can be considered as substantially equal to the distance R from the sheath axis AX to the location of the control wire 150, as illustrated in FIGS. 3B and 4A, for example. However, the maximum bending angle theta could also be determined from other conditions, such as a maximum allowable bending for the bendable hinges 122 of inner body 120 to be within the elastic bending condition. The maximum bending angle theta could also be determined from the stiffness of the hinges 122 in inner body 120.

Once the maximum bending angle theta has been established, the number of required nodes N for a given degree of curvature can be easily determined from basic geometry. For example, the number of node rings required for a 90 degree curve is given by expression (19), as follows:

$$N = \pi/(2\theta) \tag{19}$$

Now, turning to FIG. 7, it can be seen that the smallest radius of curvature $C_r$ for a sheath 100 having a number N of node rings 10 disposed at a pitch P can be determined from expression (20), as follows:

$$C_r = 2N \cdot P/\pi \tag{20}$$

The analysis and calculations of expressions (18) through (20) with reference to FIGS. 6 and 7 in conjunction with conditional expressions (10), (15) and (16) can be used to implement mechanical structures of intricate articulated sheaths with any number bending sections. Moreover, sheaths having sections of different lengths and with adjustable and different bending radius can be implemented.

To implement the foregoing concepts of the mechanical sheath 100 in practical applications, such as robotic actuated endoscopic surgical tools, one would consider positioning and orientation of an end effector based on the overall work exerted by the entire sheath or a section thereof. To that end, the foregoing concepts, in particular mathematical expressions (1) through (17) would be applied in a piece-wise manner, for example, with forward kinematic mapping (FKM) to each section being bent. Herein it is assumed that persons having ordinary skill in the field to which this application pertains would be familiar with the concepts of FKM. For that reason, only a short description is provided as to a generalized manner in which FKM would apply to the various embodiments of the mechanical sheath disclosed herein.

Specifically, for accurately mapping the kinematic effect of a tension force applied by an actuator at a proximal end of a sheath section having a predetermined number of N node rings, the resultant curvature and direction of bending can be obtained by applying piece-wise calculations to each of the ring nodes 1 to N. In this manner, FKM would transfer the tension applied to a wire to bending parameters of a sheath section by taking into account friction forces at each joint of two consecutive rings nth and (n+1)th. To simplify calculations, a constant coefficient of friction may be assumed.

From equations (18) through (20) and FIGS. 5-7 above, it was shown that the number of required nodes N for a given degree of curvature can be easily determined from basic geometry. To map the tension applied at the distal end of a sheath by an actuator to a guide wire, the number of nodes and curvature of bending could be known from the above theory. Then FKM would be applied by analytical frame transformation. For example, by defining a homogeneous transformation matrix M for each cell of n consecutive joined node rings, and parameterizing arc parameters for any number of m sections of sheath the tension applied at the proximal end of the sheath can be used to calculate the position and orientation of the distal end. For example, FKM for one section of sheath consisting of three cells in FIG. 7, may be calculated as:

$$M_1^4 = M_1^2 \cdot M_2^3 \cdot M_3^4 \tag{21}$$

On the left hand side of expression (21), the subscript 1 denotes the proximal end coordinate system and the superscript 4 is the distal end coordinate system. On the right hand side of expression 21, the first term represents the transformation matrix of the joint between node rings 1 and 2, the second term represents the transformation matrix of the joint between node rings 2 and 3, and so forth. Therefore, the resultant left hand side of expression, $M_1^4$, represents the homogeneous transformation matrix of the coordinate system 4, based on the coordinate system 1 of the proximal end.

Figure 8:
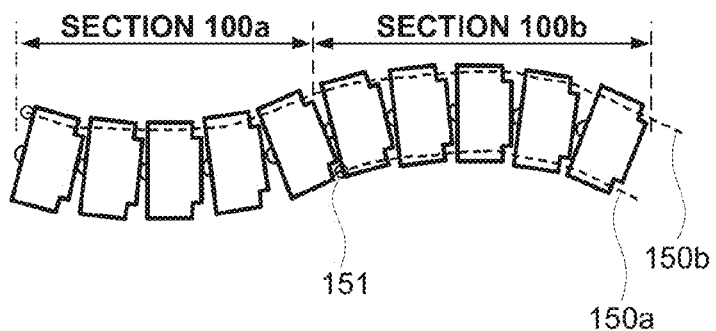
FIG. 8 illustrates an example of an articulated sheath configured to be bent into at least two consecutive curved sections.

FIG. 8 illustrates an example of a sheath 100 configured to be bent into at least two consecutive curved sections. In the example shown in FIG. 8, the sheath 100 includes a distal sheath section 100a (distal section 100a) and a proximal sheath section 100b (proximal section 100b). The distal section 100a is serially connected to the proximal section 100b. Specifically, the distal end of the proximal section 100b is connected to the proximal end of the distal section 100a. The inner body 120 (not shown) is preferably one single entity through the two sheath sections 100a and 100b. The distal section 100a includes a control wire 150b secured to a distal node ring 10 by a bead 151. The wire 150b extends from the distal node ring 10 of distal section 100a through holes 14 to the proximal end of the distal section 100b. Pulling the control wire 150b will bend the distal section 100a in a first direction in a manner similar to the basic section of sheath 100 illustrated in FIG. 5. On the other hand, a control wire 150a is secured via a bead 151 to a distal node ring 10 of the proximal section 100b. The wire 150b extends from the distal node ring 10 of the proximal section 100b to the proximal end of the proximal section 100b. Pulling the wire 150a will bend the proximal section 100b in a second direction different than the first direction of the distal section 100a. In this manner a sheath 100 having at least sections each configured to be bent in a different direction and with an adjustable radius of curvature can be implemented.

While each of the two sheath sections 100a and 100b can be controlled by only one control wire 150, as described in reference to FIG. 8, a more accurate and precise control of bending may be achieved when each of sections 100a and 100b is controlled by a pair of control wires 150.

Figure 9:
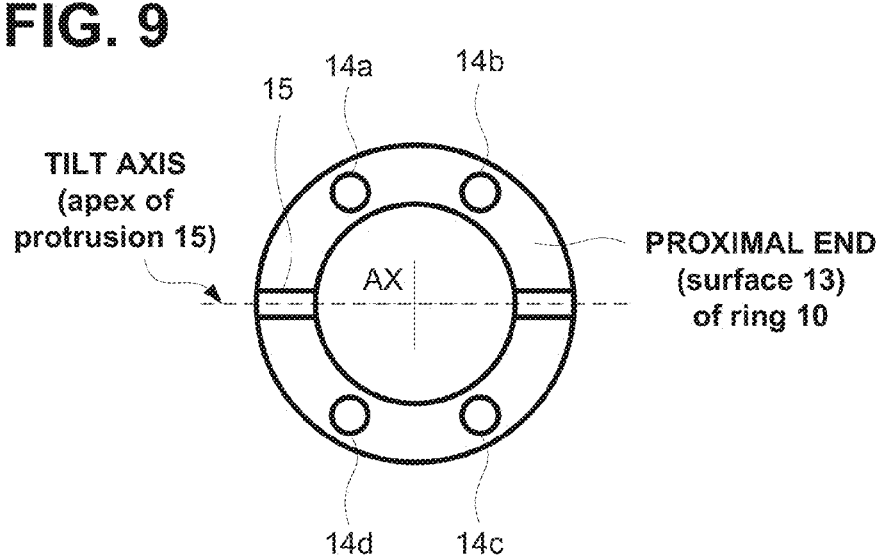
FIG. 9 illustrates a plane view of a node ring having a plurality of holes for passing therethough a corresponding plurality of control guide wires.

More specifically, FIG. 9 illustrates an example of the manner in which each node ring 10 in sheath sections 100a and 100b of FIG. 8 can be implemented, so that each section can be selectively controlled with two control wires 150. In FIG. 9, a plane view of a node ring 10 is shown in the direction of the sheath axis AX. In this configuration, a node ring 10 includes at one end thereof a flat surface 13 with curved protrusions 15 and four through-holes 14a, 14b, 14c and 14d which extend along the cylindrical wall of node ring 10. Wires 150 passing through through-holes 14a and 14d are used for control of distal section 100a, and wires passing through through-holes 14b and 14c are used for control of proximal section 100b. Alternatively, wires in through-holes 14a and 14c may be used for control of distal structure 100a and wires in through-holes 14b and 14d may be used for control of proximal section 100b. As illustrated in the plane view of FIG. 9, through-holes 14a to 14d and control wires 150 passing therethrough may be disposed anywhere on the cylindrical wall of the ring 10 other than a tilt axis (or contact line) of the curved protrusions 15. In particular, it should be noted that due to the momentum necessary for bending the inner spring of the sheath 100, the more distance from the tilt axis, the less tension is required on the control wires 150 for achieving a minimum of bending.

Naturally, based on the foregoing description, those of ordinary skill in the art will understand that a sheath 100 with any number of basic sections 100a, 100b, etc., may be implemented. To that end, however, it is required that the bending of each sheath section be preferably controlled by a separate control wire 150. Therefore, a sheath consisting of n sheath sections would require at least n+1 control wires. In which case, each wire could be configured to control the bending of each sheath section to a different direction and degree (curvature) of bending. More preferably, however, a sheath 100 consisting of n sheath sections would require 2*n control wires for more accurate and efficient bending control.

Figure 10:
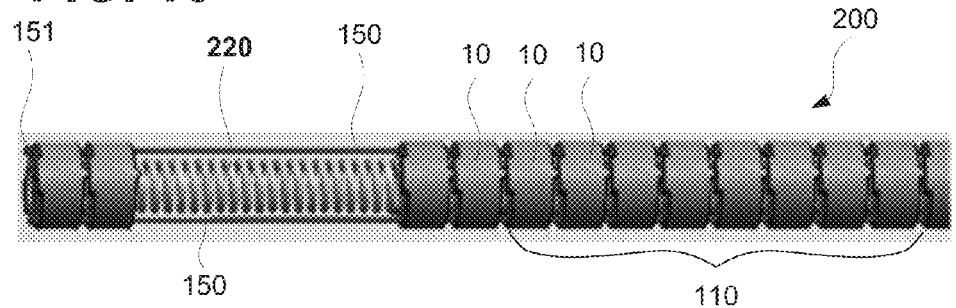
FIG. 10 illustrates an articulated sheath according to a second embodiment.

FIG. 10 illustrates a sheath 200 (articulated sheath apparatus) according to a second embodiment. Articulated sheath 200 is structurally similar to sheath 100 described in the first embodiment, except for the structure of the inner body or center spring. Specifically, in FIG. 10, the sheath 200 includes an inner body which is formed of a coil spring 220. As in the first embodiment, the coil spring 220 is arranged inside the plurality of node rings 10. Therefore, the node rings 10 are arranged around the center coil spring 220 such that consecutive node rings contact each other at a contact plane orthogonal to the linear axis AX, which coincides with the axial center of the coil spring 220 and the longitudinal axis of each node ring 10.

Figure 11A:
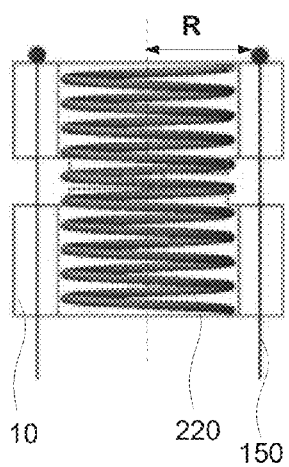
FIGS. 11A and 11B illustrate a center spring coil of the articulated sheath according to a second embodiment.
Figure 11B:
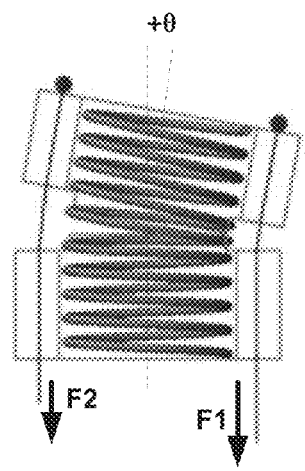

In one implantation of the second embodiment illustrated in FIG. 10, the coil spring 220 may be a single coil of sterilized rubber, plastic, steel or shape memory alloys (SMRs). The coil spring 220 preferably extends from the distal end to the proximal end of the entire sheath 200. With this implementation, the coil spring 220 needs not be longitudinally aligned with specific longitudinal positions of consecutive node rings 10. Specifically, as illustrated in FIG. 11A, the node rings 10 may be disposed at any position along the length of the coil spring 220. In this manner, the part of the coil spring 220 located inside each node ring 10 will not be bent, but the section of the coil spring 220 disposed between two consecutive node rings 10 will easily bend due to the roll (or slippage) of curved protrusion 15 over flat surface 11, as illustrated in FIG. 11B. For this embodiment, the ideal configuration for the contact line of the outer rings is at the midpoint of coil part that is not covered by the outer rings. An example of how to achieve this configuration is to have the height of the flat plane protrusion 11 and the height of the curved protrusion 15 to be the same.

Indeed, to facilitate a more efficient bending, each node ring 10 may be modified to have the curved protrusion 15 in the form of a hemispherical protrusion, as shown in FIG. 12. In this manner, since the curved protrusion 15 and the flat protrusion 11 contact each other at a small surface section (ideally at only one point), the contact portion can be reduced to a contact point. This, in turn, reduces the friction between the two consecutive node rings of a given joint, and thus makes the bending of sheath 100 more efficient. Moreover, to yet further reduce friction and increase efficiency, the flat protrusion 11 can also be made into a curved protrusion, such that the hemispherical protrusions in ring 10 may contact a curved surface instead of a flat surface.

Other alternatives for the contact portion include knife edge and pin point protrusions, in addition to the hemispherical protrusions.

Figure 13:
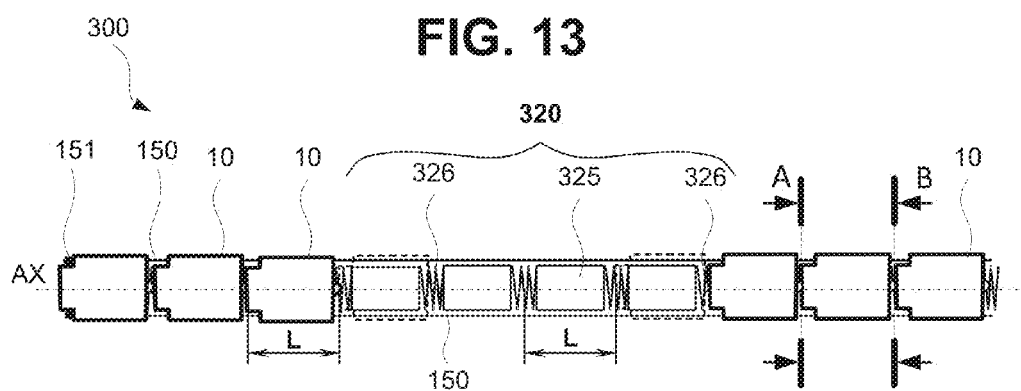
FIG. 13 illustrates a different implementation of an articulated sheath, in accordance with a third embodiment of the present invention.

FIG. 13 shows a different implementation of an articulated sheath 300, in accordance with a third embodiment of the present invention. In the embodiment of FIG. 13, the structure of sheath 300 is substantially similar to the structure of sheath 100 descried above in reference to the first embodiment. In FIG. 13, however, a center spring 320 is composed of cylindrical body rings 325 (cylindrical units) and coil springs 326 which act as bendable hinges. Thus, the articulated sheath 300 includes the center spring 320 which acts as the position restoring component. The center spring 320 is encased within a plurality of node rings 10. The node rings 10 are arranged in series and in contact with each other at a contact portion. To maintain the sheath 300 in its arranged resting state, control wires 150 attached the distal end are manipulated by an actuator (not shown) disposed at the proximal end of sheath 300. The node rings 10 include cylindrical protrusion 15 on one end-surface thereof, and a planar or flat protrusion 11 on the other end. The distance between the contact line of the cylindrical protrusion and the flat protrusion 11 defines the length L of each of node rings 10. The pitch P of each segment (cylindrical unit plus hinge) of the center spring 320 is equal to the length L of the node rings 10.

In this embodiment, the node rings 10 are engaged with the center spring 320 in a manner similar to that shown and described in the first embodiment. Specifically, cylindrical body rings 325 (cylindrical units) are linked to each other by coil springs 326. Coil springs 326 act as bendable hinges when the sheath 300 is bent. That is the inner spring 320 may be formed of a plurality of cylindrical coil units linked together by spring linking portions (hinges) located at a pitch P equal to the length L of each node ring 10. In this manner, the contact portion of the curved protrusion 15 with the flat protrusion 11 in each pair of adjacent (consecutive) node rings 10 can be arranged at the same longitudinal location in the axial direction as each center (point) of bending of the coil spring 326. The center spring 320 may be made of linked pieces of rubber tube or plastic tube linked by cylindrical units of coil spring made of SMAs, for example.

Figure 14A:
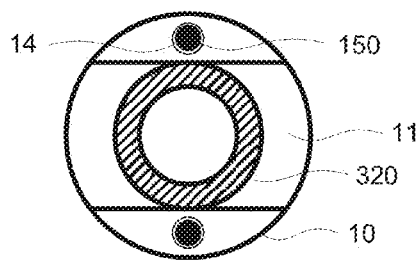
FIGS. 14A and 14B show cross-sectional views at lines A and B, respectively, of FIG. 13.
Figure 14B:
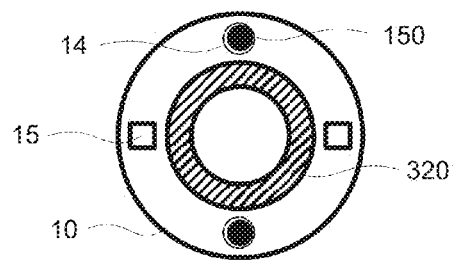

FIG. 14A shows the cross section view A of FIG. 13, and FIG. 14B shows the cross sectional view B of FIG. 13. In both FIGS. 14A and 14B, control wires 150 pass through the holes 14 of the node rings 10. The diagonal hatched portion shows the center spring 320 contained inside of node ring 10. The cylindrical protrusion 15 shown in FIG. 14B will be in direct contact with the planar protrusion 11 shown in FIG. 14A.

Figure 15:
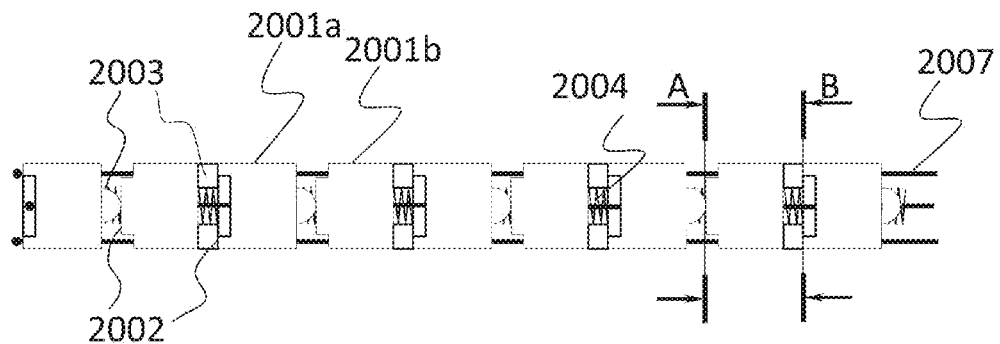
FIG. 15 illustrates a different implementation of an articulated sheath, in accordance with a fourth embodiment of the present invention.

FIG. 15 shows another embodiment where the guide wire rings are configured so that they are not confined to one bending direction as a whole and the bending of the mechanical structure can be in any one direction. The guide wire rings 2001a and 2001b are of the same shape but are positioned with 90 degrees twist with respect to each other on the lengthwise axis of the mechanical structure. In FIG. 15, cylindrical protrusions are labeled 2003 and the plane in contact are labeled 2002. The cylindrical protrusion of 2001a has the contact line to the plane of 2001b in the direction perpendicular to the plane of the figure and the contact line of the cylindrical protrusion of 2001b is orthogonal to the contact line of the 2001a. The guide wire rings are connected with 90 degree twist in alternating manner throughout the mechanical structure. The center spring 2004 of this embodiment can be a simple coil spring as in the embodiment of FIG. 8, or a structure as in FIG. 15, where the body rings are connected with coil spring. Pulling the guide wires 2007, the curvature and the direction of the mechanical structure is controlled. The center spring may also be a hollow tube with hinges cut in it such as in FIG. 2, but with hinges located 90 degrees in alternating fashion.

Figure 16A:
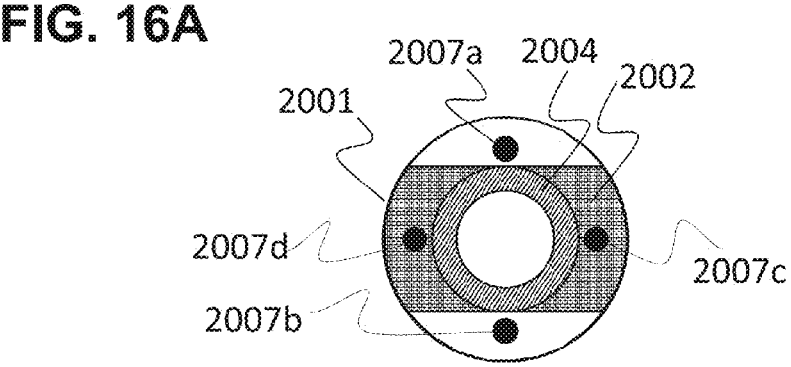
FIGS. 16A and 16B show cross-sectional views at lines A and B, respectively, of FIG. 15.
Figure 16B:
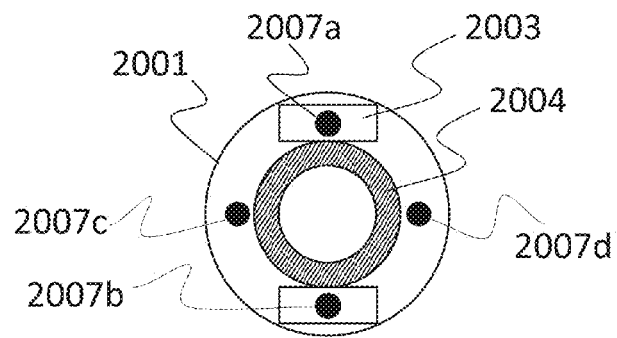

FIG. 16A and 16B show cross sectional views along cuts A and B of FIG. 15, respectively. The guide wire ring 2001 has four guide wires 2007a to 2007d through four guide wire holes. Two of them, 2007a and 2007b are going through a hole in the cylindrical protrusion 2003. Two of them are located through the plane portion 2002 which will be in contact with the cylindrical protrusion of the adjacent guide wire ring and shown with cross hatch pattern. Center coil is shown as 2004 with the diagonal hatch pattern. Pulling of the guide wires 2007a or 2007b will bend the mechanical structure to up or down within the plane of FIG. 15. Pulling of the guide wires 2007c and 2007d will bend the mechanical structure out of or into the plane of FIG. 15.

Figure 17A:
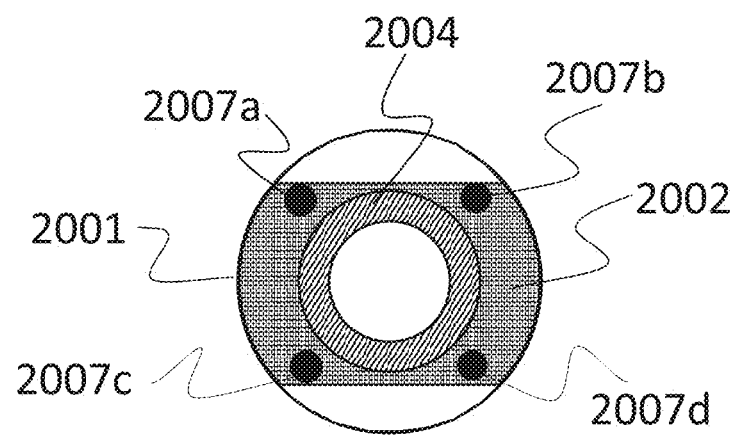
FIGS. 17A and 17B illustrate control guide wires located 45 degrees rotated with respect to those shown in FIGS. 16A and 16B.
Figure 17B:
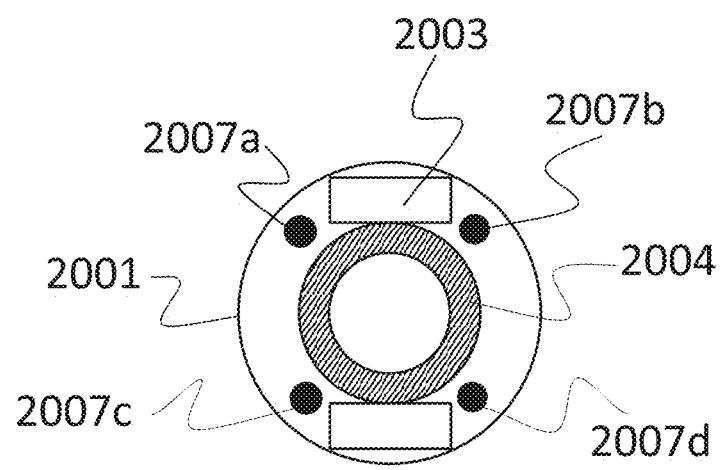

FIGS. 17A and 17B show, the guide wires may be located 45 degrees rotated with respect to those shown in FIGS. 16A and 16B. Although the configuration illustrated in FIGS. 16A and 16B provides simple control of the mechanical structure with pulling the desired wire for desired bending direction, the guide wire holes are located on the cylindrical protrusion and the plane of contact and because of that the contact line are short and the protrusion may wear out or be damaged. FIGS. 17A and 17B show the guide wires located out of phase from the cylindrical protrusions. Pulling of the wires 2007a and 2007b will bend the mechanical structure up and pulling of the wires 2007c and 2007d will bend the structure down. Pulling of the wires 2007a and 2007c or on 2007b and 2007d will bend the mechanical structure left or right.

Figure 18:
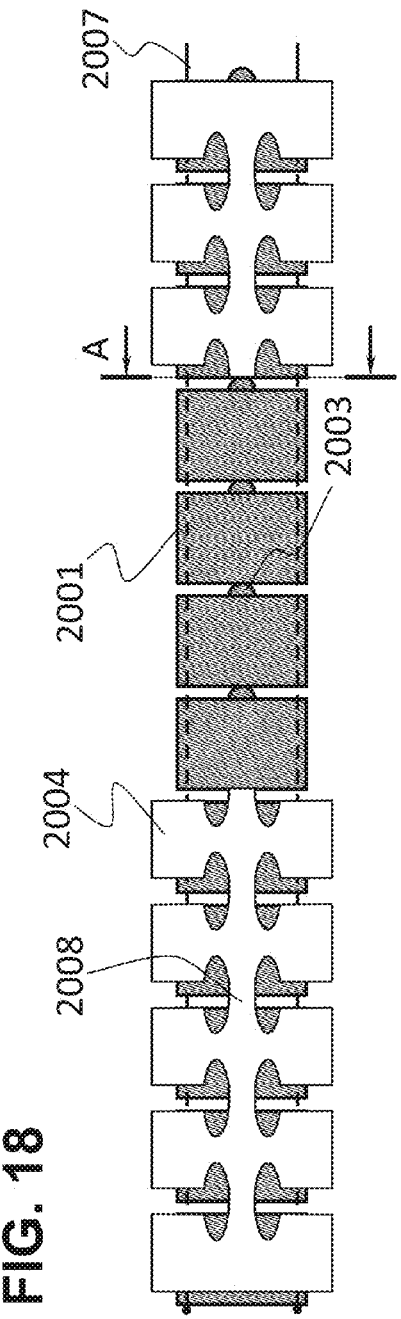
FIG. 18 illustrates a different implementation of an articulated sheath, in accordance with a fifth embodiment of the present invention.

FIG. 18 shows another configuration, as an additional embodiment with the guide wire rings positioned inside of the position restoring component. In FIG. 18, the guide wire rings 2001 are located inside of the restoring component 2004. The restoring component consists of body rings connected with hinges 2008. The guide wire rings 2001 have cylindrical protrusions 2003 at one end and plane surface on the other side. The cylindrical protrusions make contact with the plane surface of the adjacent guide wire rings. The plural guide wire rings are connected with guide wires 2007 going through them with a bead at the end. In FIG. 25 the middle portion of the restoring spring is hidden to show the inner guide wire rings with hatched pattern. The guide wires are shown with dotted lines for the middle section.

Figure 19:
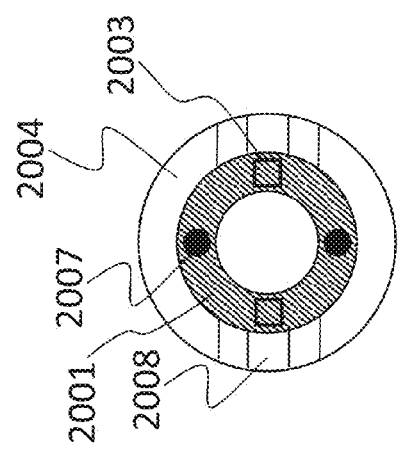
FIG. 19 shows a cross-sectional view at line A of FIG. 18.

FIG. 19 shows the cross sectional view A of FIG. 18. The guide wire ring 2001 with its cylindrical protrusion 2003 is shown in hatched pattern and located inside the restoring spring 2004. The part 2004 is the cylindrical body ring part of the spring and 2008 is the hinges that bend and connect the body ring parts. The guide wires 2007 are shown at the top and bottom of the guide wire rings.

Figure 20:
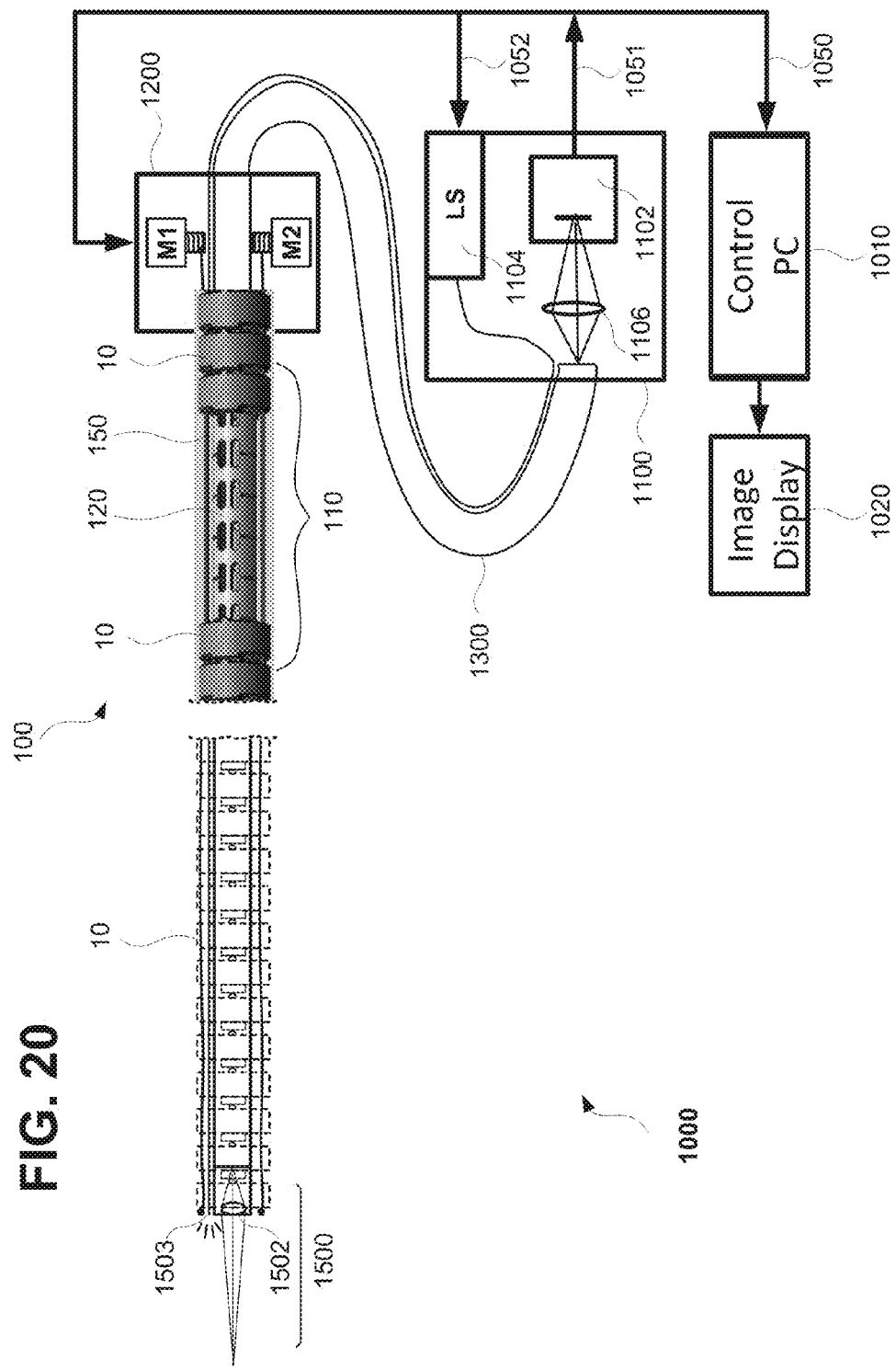
FIG. 20 illustrates an embodiment of an endoscopic system, in accordance with an exemplary application of any of the embodiments of the present invention.

FIG. 20 shows an embodiment of an endoscopic system 1000, in accordance with an exemplary application of any of the embodiments of the present invention. The endoscope unit includes a bundle fiber, an illumination fiber, an illumination source, imaging lenses, an imaging sensor, and an image display. The illumination source and imaging sensor with its lens is in a proximal unit. The illumination light from the illumination source of the proximal unit is sent by an illumination fiber incorporated in the endoscope unit. At the distal end is an imaging lens which images the subject to the end of the bundle fiber. The bundle fiber transfers the image to the proximal end of the fiber and another lens images the end of the fiber to the imaging sensor. The image is sent to image display. The articulated sheath has a sheath control box at the proximal end of the sheath and is connected to the control PC. The control PC will send signal to the sheath control to pull the respective wires to control the sheath shape. Although it is not shown in FIG. 20, an endoscope unit often has another port (a channel) for sending surgical assist tools (end effectors) to the distal end of the sheath 100. Examples of end effectors are a clipping tool or an ablation tool, and other surgical tools.

More specifically, the endoscopic system 1000 includes an imaging endoscope which is inserted in the articulated sheath 100. An actuator circuit 1200 includes a plurality of actuator units M1 and M2 configured to control end effectors attached at the distal end of sheath 100. The endoscope includes bundle fiber 1300, which includes at least an illumination fiber and a light collection fiber. An imaging system 1100 includes an illumination source LS 1104, an image sensor 1102 and a light collimating unit 1106. A personal computer PC 1010 serves as a control and processing unit configured to control each aspect of the endoscopic system 1000. For example, control PC 1010 is connected via a network link 1050 to the actuator circuit 1200 to control the above-mentioned endoscope and end effectors. The control PC 1010 is also connected to the imaging system 1100 via a network link 1052, and can control the illumination light source LS 1104 as well as the image sensor 1102. In operation, the control PC 1010 control the light source LS 1104 to provide illumination light at the distal end of sheath 100 via an illumination fiber 1503. During operation of the endoscopic system 1000, an endoscopist or surgeon can use the sheath 100 to introduce and guide end effectors to a desired position in the interior of a patient. Control and guidance of end effectors may be performed either manually via the actuator circuit 1200, or automatically based on robotic algorithms executed by control PC 1010. The imaging unit 1500 includes light collection lenses, which serve to form an image of an object scene. The image of the object scene is transmitted through the sheath 100 via the fiber bundle 1300. The imaging sensor 1102 detects the image of the object scene, and the control PC processes the detected image. An image display 1020 serves to visually inform the endoscopist and/or surgeon of the actions performed by end effectors attached at the distal end of sheath 100, as well as to display images captured by the light detection unit 1500.

<Other Embodiments and Modifications>

In the embodiments disclosed above, various combinations and modifications will be readily evident to persons having ordinary skill in the art. For example, as illustrated in FIG. 20, the endoscopic system 1000 includes an imaging endoscope which is inserted in the articulated sheath 100. In FIG. 20, the actuator circuit 1200 is directly connected to the proximal end of the articulated sheath 100 and the imaging unit 1500 is connected at the distal end of the articulated sheath 100. However, the application of the articulated sheath is not limited to this example.

Figure 21A:
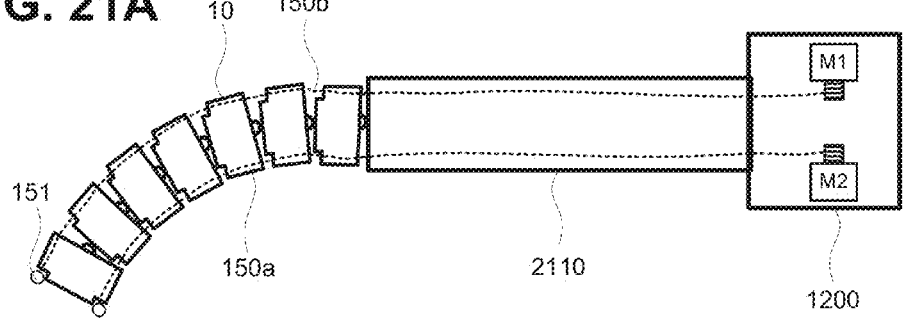
FIGS. 21A, 21B and 21C illustrate some examples of certain modifications to the articulated sheath, in accordance with the present invention.
Figure 21B:
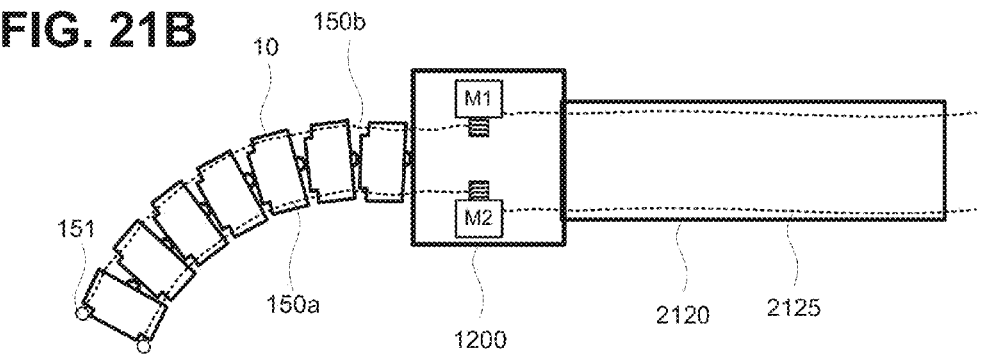
Figure 21C:
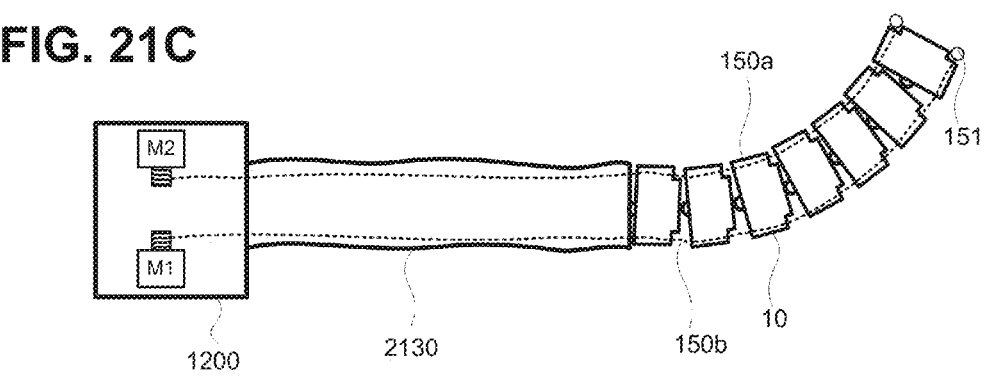

Turning now to FIGS. 21A, 21B and 21C some examples of certain modifications to the articulated sheath are described. In FIG. 21A, as another embodiment of the present invention, it can be assumed that the endoscopic system has a rigid tubular part 2110. For example, when applied to the endoscopic system 1000 of FIG. 20, the tubular part 2110 is attached at the proximal end of the articulated sheath, so as to reach certain distance inside of the subject under examination. The control of the articulated sheath at the tip of the tubular part 2110 still can be executed with the circuit controller 1200 via guide wires 150*a* and 150*b*. In FIG. 21A, the most proximal node ring 10 is made to be longer than the pitch of the other node rings 10 so at to form the straight tubular part 2110. A typically length of the straight tubular part 2110 may be approximately 20 cm for certain applications, but it may vary depending on the desired use. Similarly, the inner spring (not shown in FIG. 21A), which is the restoring force component, has no hinges and is not able to bend for the same length as the tubular part 2110. Notably, the tubular part 2110 can still maintain the same holes 14 configured as in the other node rings 10. In this manner, when the guide wires 150*a* and 150*b* are pulled, the mechanical structure of the articulated sheath at the tip of the straight tubular part 2110 will be controlled without bending the tubular part 2110. In FIG. 21A, the actuator circuit 1200 is mounted at the proximal end of the straight tubular part 2110. In this case, the tubular part 2110 may be fabricated with certain volume to provide housing for the controller circuit 1200 such that it can also function as handling grip for the operator to hold the articulated sheath.

FIG. 21B illustrates an additional modification of the articulate sheath in which the controller circuit 1200 is located between the articulated sheath and a tubular part 2120. In the arrangement shown in FIG. 21B, the controller circuit 2100 is preferably of a reduced size. The tubular part 2120 may include holes similar to holes 14 of node rings 10. This will allow electrical connections 2125 to be delivered to the actuator circuit 2100. Depending on the application, the tubular part 2110 in FIG. 21A or the tubular part 2120 in FIG. 21B is not limited to a straight structure, but it may have a preconfigured shape or curvature for ease of operation.

FIG. 21C illustrates another modification to the articulated sheath disclosed herein. In FIG. 21C, it can be assumed that the endoscopic system has a soft flexible tubular part 2130. The flexible tubular part 2130 should have enough stiffness so that the pulling of the wires 150*a* and 150*b* will not change the shape of the flexible part 2130, but should be flexible to accommodate to the shape of certain channels. For example, the flexible tubular part 2130 can be flexible enough to accommodate its shape to the gastrointestinal (GI) tract without the need of the actuator controller, but at the same time it should be stiff so that the wires 150*a* and 150*b* traveling though it can actuate on the node rings 10 to actuate on the shape of the articulated sheath. To that end, the soft flexible tubular part 2130 is attached at the proximal end of the articulated sheath, so as to reach certain distance inside of the subject in a freely movable state according to the subject's shape. The control of the mechanical structure of the articulate sheath at the tip of the flexible tubular part 2130 is still achieved by the circuit controller 1200. In FIG. 21C, the most proximal ring is attached to a flexible tubular part 2130. Similarly, the inner spring (not shown in FIG. 21C), which is the restoring force component, is attached to a flexible tube for the same length as the flexible tubular part 2130.

The length of the flexible tubular part 2130 can be determined by the desired application. The outer flexible tubular part 2130 preferably has the same holes 14 as in the node rings 10, so that when the guide wire 150*a* and 150*b* are pulled, the mechanical structure at the tip of the tubular part 2130 will be controlled. The actuator circuit 1200 may be mounted at the proximal end of the flexible tubular part 2130, as in the arrangement shown in FIG. 21B. In that case, the actuator circuit 1200 is mounted at the distal end of the flexible tubular part 2130 and at proximal end of the articulated sheath, so as to control the bending without changing the flexible part. The outer long flexible tube part has the electric cables (see 2125 in FIG. 21B) to send signals to the actuator circuit 1200.

Although not shown in the figures of all embodiments, the mechanical structure of sheath 100 may further include an sterilized cover tube or cover lining disposed over the node rings 10 to prevent the entering of materials foreign, such as liquids or objects from the ambient environment, and also to avoid contact of the mechanical structure with delicate organs or tissue of a patients' body part.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

What is claimed is:

1. A sheath apparatus comprising: a plurality of node rings configured to be tilted with respect to each other, each node ring defining a substantially cylindrical wall and having at least one hole passing through said cylindrical wall, the plurality of node rings being arranged next to each other along a central axis such that consecutive node rings contact each other at a contact plane; a manipulating wire going through the holes in said stacked node rings; and a position restoring component including a plurality of cylindrical units connected to each other by a bendable elastic link, wherein the stiffness of the bendable elastic link smaller that stiffness of each cylindrical unit, and wherein the contact plane of said stacked node rings is located at a substantially same location along the central axis as a bending point of said bendable elastic link, in the position restoring component, the position restoring component is configured to restore said stacked node rings from a tilted position to an original position, and has a stiffness in a bending direction that is smaller than a stiffness in the direction orthogonal to the bending direction and the central axis;

wherein said position restoring component is located inside or outside of the stacked node rings.

2. The sheath apparatus according to claim 1, wherein a distance e between the contact plane of said two consecutive stacked node rings and a bending point of said position restoring component along the central axis is smaller than $R\mu$, where R is a distance from the central axis to the manipulating wire and μ is the friction coefficient at a point of contact said two consecutive stacked node rings.

3. The sheath apparatus according to claim 2, wherein a distance ϵ between the contact plane of said two consecutive stacked node rings and a bending point of said position restoring component along the central axis is smaller than R/10μ, where R is a distance from the central axis to the manipulating wire and μ is the friction coefficient at a point of contact said two consecutive stacked node rings.

4. The sheath apparatus according to claim 1, further comprising a plurality of mechanical sheath sections, wherein each of the plurality of mechanical sheath section comprise:
a plurality of node rings configured to be tilted with respect to each other, each node ring defining a substantially cylindrical wall and having at least one hole passing through said cylindrical wall, the plurality of node rings being arranged next to each other along a central axis such that consecutive node rings contact each other at a contact plane;
a manipulating wire going through the holes in said stacked node rings; and
a position restoring component configured to restore said stacked node rings from a tilted position to an original position,
wherein said position restoring component is located inside of the stacked node rings, and
wherein at least one of said manipulating wire is attached to the distal ends of each of the mechanical sheath sections.

5. The sheath apparatus according to claim 4, wherein a contact portion of said stacked node ring are the same location in the axial direction as bending center of said restoring component.

6. The sheath apparatus according to claim 5, wherein a distance c between the contact plane of said two consecutive stacked node rings and a bending point of said position restoring component along the central axis is smaller than R/μ, where R is a distance from the central axis to the manipulating wire and μ is the friction coefficient at a point of contact said two consecutive stacked node rings.

7. The sheath apparatus according to claim 6, wherein a distance c between the contact plane of said two consecutive stacked node rings and a bending point of said position restoring component along the central axis is smaller than R/10μ, where R is a distance from the central axis to the manipulating wire and μ is the friction coefficient at a point of contact said two consecutive stacked node rings.

8. The sheath apparatus according to claim 1, wherein the bending point of said position restoring component is located on the contact plane.

9. The sheath apparatus according to claim 1, wherein said position restoring component includes a bendable spring with a plurality of links disposed at a pitch equal to a length of each stacked node ring.

\* \* \* \* \*